US012357655B2

(12) United States Patent
Komorowski

(10) Patent No.: US 12,357,655 B2
(45) Date of Patent: *Jul. 15, 2025

(54) POLYGLUTAMIC ACID COMPOSITIONS AND METHODS OF USING

(71) Applicant: Bonafide Health, LLC, Harrison, NY (US)

(72) Inventor: James R. Komorowski, Trumbull, CT (US)

(73) Assignee: Bonafide Health, LLC, Harrison, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/177,720

(22) Filed: Mar. 2, 2023

(65) Prior Publication Data

US 2023/0277581 A1 Sep. 7, 2023

Related U.S. Application Data

(60) Provisional application No. 63/315,964, filed on Mar. 2, 2022.

(51) Int. Cl.

| *A61K 31/785* | (2006.01) |
|---|---|
| *A61K 9/00* | (2006.01) |
| *A61K 9/02* | (2006.01) |
| *A61K 31/765* | (2006.01) |
| *A61K 47/10* | (2017.01) |
| *A61K 47/14* | (2017.01) |
| *A61K 47/26* | (2006.01) |
| *A61P 15/02* | (2006.01) |
| *A61P 15/12* | (2006.01) |

(52) U.S. Cl.
CPC .......... *A61K 31/785* (2013.01); *A61K 9/0034* (2013.01); *A61K 47/10* (2013.01); *A61K 47/14* (2013.01); *A61K 47/26* (2013.01)

(58) Field of Classification Search
None
See application file for complete search history.

(56) References Cited

U.S. PATENT DOCUMENTS

| 6,190,693 B1 * | 2/2001 | Kafrissen ................ A61P 15/12 424/464 |
|---|---|---|
| 2009/0253705 A1 | 10/2009 | Berger et al. |
| 2012/0035118 A1 | 2/2012 | Caltabiano et al. |
| 2019/0151392 A1 | 5/2019 | Seipel |
| 2019/0247428 A1 | 8/2019 | Chung |
| 2020/0085857 A1 | 3/2020 | Choi et al. |
| 2021/0213087 A1 | 7/2021 | Komorowski et al. |
| 2022/0202840 A1 | 6/2022 | Sigurdsson |

FOREIGN PATENT DOCUMENTS

| CN | 103800219 A | * | 5/2014 | |
|---|---|---|---|---|
| CN | 105255173 B | | 9/2017 | |
| CN | 109123032 | | 1/2019 | |
| KR | 2018040906 A | * | 4/2018 | ............ A23L 33/10 |
| WO | WO-2012/018773 | | 2/2012 | |
| WO | WO-2022/158504 | | 7/2022 | |
| WO | WO 2023/168365 | | 9/2023 | |
| WO | PCT/US2023/035433 | | 10/2023 | |

OTHER PUBLICATIONS

Google English translation of CN103800219A. (Year: 2014).*
Chapel Hill Gynecology, "Can you prevent early menopause", retrieved from on-line website: https://chapelhillgynecology.com/can-you-prevent-early-menopause/, 2022, pp. 1-6. (Year: 2022).*
Edwards et al., "Treating vulvovaginal atrophy/genitourinary syndrome of menopause: how important is vaginal lubricant and moisturizer composition?", Climacteric, Mar. 3, 2016; 19(2): 151-161 (Year: 2016).*
Cooper et al., "Active agents, biomaterials, and technologies to improve biolubrication and strengthen soft tissues," Biomaterials 181 (2018) pp. 210-226 (Year: 2018).*
Ogunleye et al., "Poly-gamma-glutamic acid: production, properties and applications," Microbiology (2015), 161, 1-17 (Year: 2015).*
Rosano et al., "Menopause and cardiovascular disease: the evidence," Climacteric, vol. 10, 2007—Issue sup 1 (abstract is only attached). (Year: 2007).*
Kumar et al., "Poly-gamma-glutamic acid: a promising biopolymer", Defense Life Science Journal, vol. 3, No. 3, Jul. 2018, pp. 301-306. (Year: 2018).*
Livengood, "Bacterial Vaginosis: An Overview for 2009", MedReviews, 2009, pp. 28-37 . (Year: 2009).*
Muhleisen et al., "Menopause and the vaginal microbiome", Maturitas 91, (2016), pp. 42-50. (Year: 2016).*
KR20180040906A English Translation (Year: 2018).*
U.S. Appl. No. 18/381,087, filed Oct. 17, 2023, Komorowski.
U.S. Appl. No. 18/381,558, filed Oct. 18, 2023, Komorowski et al.
Gennaro, Alfonso R., and Joseph P. Remington: *Remington: The Science and Practice of Pharmacy* . 20th ed., Lippincott Williams & Wilkins, 2000.
Fitzmaurice, G. M., Laird, N. M., & Ware, J. H. (2011). *Applied Longitudinal Analysis* (2nd. ed.). Hoboken, New Jersey.: John Wiley & Sons, Inc.
Bottiglieri, "SAMe (S-Adenosyl-Methionine) Metabolic Function and Health Benefits," Medizioni, 2019: pp. 33-53.
Bright et al., "Developing and Validating the International Consultation on Incontinence Questionnaire Bladder Diary," European Urology, 2014: 66(2): pp. 294-300.
Brooks et al., "Beneficial effects of Lepidium meyenii (Maca) on psychological symptoms and measures of sexual dysfunction in postmenopausal women are not related to estrogen or androgen content," Menopause, 2008; 15(6): pp. 1157-1162.
Cleveland Clinic, "Overactive Bladder," [online], 2022, [retrieved on Oct. 24, 2023]. Retrieved from the Internet: <URL: https://my.clevelandclinic.org/health/diseases/14248-overactive-bladder>.

(Continued)

*Primary Examiner* — Kyung S Chang
(74) *Attorney, Agent, or Firm* — Arnall Golden Gregory LLP

(57) ABSTRACT

Disclosed herein are compositions comprising one or more polyglutamic acid compounds. The compositions are for treating, ameliorating, preventing, or reducing the symptoms of vaginal dryness and the symptoms associated with menopause. Also described herein are suppository formulations of the compositions.

22 Claims, No Drawings

(56) References Cited

OTHER PUBLICATIONS

Coyne et al., "The validation of the patient perception of bladder condition (PPBC): a single-item global measure for patients with overactive bladder," Eur Urol, 2006; 49(6): pp. 1079-1086.

Erdem et al., "Management of overactive bladder and urge urinary incontinence in the elderly patient," Am J Med, 2006; 119(3 Suppl 1): pp. 29-36.

Gonzales, "Ethnobiology and Ethnopharmacology of *Lepidium meyenii* (Maca), a Plant from the Peruvian Highlands," Evidence-Based Complementary and Alternative Medicine, 2012; Article ID 193496, 10 pages.

Homma et al., "Symptom assessment tool for overactive bladder syndrome—overactive bladder symptom score," Urology, 2006; 68(2): pp. 318-323.

Hutchinson et al., "Overactive bladder syndrome: Management and treatment options," Aust J Gen Pract, 2020; 49(9): pp. 593-598.

Kadakia et al., "Phase II evaluation of S-adenosyl-L-methionine (SAMe) for the treatment of hot flashes," Support Care Cancer, 2016; 24(3): pp. 1061-1069.

Kumar et al., "Poly-γ-glutamic acid: A Promising Biopolymer," Defense Life Science Journal, 2018; 3(3): pp. 301-306.

Mansfield, "Muscarinic receptor antagonists, the overactive bladder and efficacy against urinary urgency," Clinical Medicine Insights: Therapeutics, 2010; 2: pp. 471-480.

Matza et al., "Test-retest reliability of four questionnaires for patients with overactive bladder: the overactive bladder questionnaire (OAB-q), patient perception of bladder condition (PPBC), urgency questionnaire (UQ), and the primary OAB symptom questionnaire (POSQ)," Neurourol Urodyn, 2005; 24(3): pp. 215-225.

Mayo Clinic, "Overactive Bladder", [online], 2022, [retrieved on Oct. 24, 2023]. Retrieved from the Internet: <URL: https://www.mayoclinic.org/diseases-conditions/overactive-bladder/symptoms-causes/syc-20355715>.

Mayo Clinic, "SAMe", [online], 2020, [retrieved on Oct. 24, 2023]. Retrieved from the Internet: <URL: https://www.mayoclinic.org/drugs-supplements-same/art-20364924>.

Meissner et al., "Hormone-Balancing Effect of Pre-Gelatinized Organic Maca (Lepidium peruvianum Chacon): (III) Clinical responses of early-postmenopausal women to Maca in double blind, randomized, Placebo-controlled, crossover configuration, outpatient study," Int J Biomed Sci, 2006; 2(4): pp. 375-394.

Salmaggi et al., "Double-blind, placebo-controlled study of S-adenosyl-L-methionine in depressed postmenopausal women," Psychother Psychosom, 1993; 59(1): pp. 34-40.

Schoendorfer et al., "Urox containing concentrated extracts of *Crataeva nurvala* stem bark, *Equisetum arvense* stem and *Lindera aggregata* root, in the treatment of symptoms of overactive bladder and urinary incontinence: a phase 2, randomised, double-blind placebo controlled trial," BMC Complement Altern Med, 2018; 18(1): p. 42.

Symonds et al., "Development of a questionnaire on sexual quality of life in women," J Sex Marital Ther, 2005; 31(5): pp. 385-397.

U.S. Department of Health and Human Services, FDA, "Guidance for Industry: Q3C Impurities: Residual Solvents," Dec. 1997.

Yamanishi et al. "The role of M2-muscarinic receptors in mediating contraction of the pig urinary bladder in vitro", British Journal of Pharmacology, 2000; 131: pp. 1482-1488.

Yu et al., "Development of short forms from the PROMIS™ sleep disturbance and Sleep-Related Impairment item banks," Behav Sleep Med, 2011; 10(1): pp. 6-24.

Berlanga et al., "Efficacy of S-Adenosyl-L-Methionine in Speeding the Onset of Action of imipramine," Psychiatry Res., 1992; 44(3): pp. 257-262.

Francioso et al., "Pharmacokinetic properties of a novel formulation of S-adenosyl-L-methionine phytate," Amino Acids, 2021; 53: pp. 1559-1568.

Hedge, "Muscarinic receptors in the bladder: from basic research to therapeutics," British Journal of Pharmacology, 2006; 147(6): pp. S80-S87.

International Search Report and Written Opinion issued in PCT/US2023/035433, mailed Feb. 2, 2024.

International Search Report and Written Opinion issued in PCT/US2023/063620, mailed May 31, 2023.

Raskin et al., "Can an Apple a Day Keep the Doctor Away?" Current Pharmaceutical Design, 2004; 10: pp. 3419-3429.

Tallarida, "Quantitative Methods for Assessing Drug Synergism," Genes & Cancer, 2011; 2(11): pp. 1003-1008.

International Search Report and Written Opinion issued in PCT/US2024/046732, mailed Dec. 23, 2024.

* cited by examiner

POLYGLUTAMIC ACID COMPOSITIONS AND METHODS OF USING

CROSS-REFERENCE TO RELATED APPLICATIONS

This application claims priority to U.S. Provisional Application No. 63/315,964 filed on Mar. 2, 2022, the disclosure of which is incorporated herein by reference in its entirety.

BACKGROUND

Vaginal dryness is a common condition that can affect women of all ages. However, vaginal dryness is most common in women following menopause. In postmenopausal women, vaginal dryness may be associated with declining estrogen levels. Topical estrogen therapy has been the most common treatment for vaginal dryness but this therapy carries risks such as vaginal bleeding and increased risk of uterine cancer. An alternative therapy for patients unwilling or unable to consider an estrogen therapy is hyaluronic acid. Yet, it also has adverse effect including vulvovaginal candidiasis and bacterial vaginosis. As such, the prior art methods and compositions for treatment of vaginal dryness are insufficient and solutions are provided herein to help alleviate vaginal dryness.

SUMMARY

Embodiments of the present disclosure relate to novel compositions containing one or more polyglutamic acid compounds and their use in the treatment and/or amelioration of the symptoms of vaginal dryness and the symptoms associated with menopause.

These and other features, aspects, and advantages of the present embodiments will become understood with reference to the following description and appended claims.

DETAILED DESCRIPTION

Described herein are compositions comprising one or more polyglutamic acid compounds and a pharmaceutically acceptable carrier. Each polyglutamic acid compound can be prepared by reacting a glutamic ester monomer with a suitable initiator. The molecular weight of each polyglutamic acid compound is determined by the number of the glutamic acid monomers that have been linked, corresponding to an n value set forth below.

The structure of a polyglutamic acid compound is depicted below:

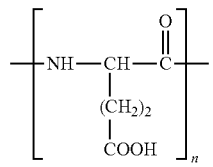

N refers to a chain length of a polyglutamic acid compound and can be between 300 and 30,000. The molecular weight of a polyglutamic acid compound of the disclosure can be between about 50 and 4,000 kDa. The composition described herein can contain one or more polyglutamic acid compounds that can have different polymer chain lengths (i.e., different n values).

For example, and without limitation, a composition can be comprised of a first polyglutamic acid compound, wherein the first polyglutamic acid compound has an n value of between about 300 and 500; a second polyglutamic acid compound, wherein the second polyglutamic acid compound has an n value between about 1,000 and 10,000; and a third polyglutamic acid compound, wherein the third polyglutamic acid compound has an n value between about 20,000 and 30,000.

The number of polyglutamic acid compounds having different n values in a composition is not particularly limited. In some embodiments, a composition can comprise one, two, three, four, five, six, or more different polyglutamic acid compounds that have different n values.

Without being bound to any particular theory, the compositions containing one or more polyglutamic acid compounds of the instant disclosure produce unexpectedly superior results due to the compounds' ability to penetrate varying layers of vaginal epithelial tissue depending upon the particular ratio of polyglutamic acid compounds having different n values. For example, a composition can comprise a first polyglutamic acid compound and a second polyglutamic acid compound, wherein the first polyglutamic acid compound has an n value that is less than the second polyglutamic acid compound. It is believed that a polyglutamic acid compound having a smaller n value is able to penetrate into deeper layers of the vaginal epithelium than a polyglutamic acid compound with a larger n value. And it is further believed that a second polyglutamic acid compound having an n value greater than a first polyglutamic acid compound will not penetrate into deeper epithelial layers, but rather, the second polyglutamic acid compound will stay closer to the surface than the first polyglutamic acid compound.

Certain embodiments comprise a first polyglutamic acid compound, a second polyglutamic acid compound, and a third polyglutamic acid compound. In certain embodiments, the first polyglutamic acid compound is a polyglutamic acid compound comprising a greater number of glutamic acid monomers than the second polyglutamic acid compound. The second polyglutamic acid compound comprises a greater number of glutamic acid monomers than the third polyglutamic acid compound. In certain embodiments, the first polyglutamic acid compound is configured to penetrate into the stratus corneum layer of a subject's vaginal wall, the second polyglutamic acid compound is configured to penetrate into the stratum *granulosum* layer of a subject's vaginal wall, and the third polyglutamic acid compound is configured to penetrate into the stratum *spinosum* layer of a subject's vaginal wall. In some embodiments, one or more of the polyglutamic acid compounds can have an n value large enough such that it does not penetrate any skin layers, but stays on the skin surface, and can act as a lubricant.

The amount of each polyglutamic acid compound in any of the compositions described herein is not particularly limited, and may be about 10 µg to about 10 g. For example, the amount can be 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or any amount therebetween.

The compositions disclosed herein can be used to treat, prevent, or alleviate vaginal dryness, vaginal itching, and/or vaginal burning. In some embodiments, the compositions described herein can be used to maintain healthy levels of vaginal moisture. In some embodiments, the compositions described herein can be used to accelerate the rate of wound healing, prevent urinary tract infections, and/or maintain pH values in a vaginal tissue. In certain embodiments, a composition as described herein is administered to a subject to avoid painful intercourse. In certain embodiments, a composition as described herein is administered to a subject to rejuvenate a vaginal tissue.

In certain embodiments, a composition can be administered to a subject's vaginal tissue to treat, prevent, ameliorate, and/or reduce the symptoms of vaginal dryness. In certain embodiments, a composition can be administered to a subject's vaginal tissue to maintain a healthy level of vaginal moisture. In certain embodiments, a composition can be administered to a subject's vaginal tissue to treat, prevent, and/or ameliorate the symptoms of vaginal dryness due to menopause. In some embodiments, a composition can be administered to a subject's vaginal tissue to treat, prevent, and/or ameliorate one or more symptoms of menopause. In certain embodiments, a composition can be administered to a subject's vaginal tissue to reduce the pain associated with sexual activity, including sexual intercourse. In certain embodiments, a composition can be administered to a subject's vaginal tissue to treat, prevent, and/or ameliorate vaginal itching. In certain embodiments, a composition can be administered to a subject's vaginal tissue to treat, prevent, and/or ameliorate vaginal burning. In certain embodiments, a composition can be used for one or more of the foregoing.

In some embodiments, the compositions disclosed herein are in the form of pharmaceutically effective salts. The phrase "pharmaceutically acceptable salt(s)," is art recognized and, as used herein includes, but is not limited to, salts of acidic or basic groups that may be present in the compositions disclosed herein. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glycerate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds present in the compositions disclosed herein that include an amino moiety also can form pharmaceutically acceptable salts with various amino acids, in addition to the acids mentioned above. Compounds present in the compositions disclosed herein that are acidic in nature are capable of forming base salts with various pharmacologically acceptable cations. Non limiting examples of such salts include alkali metal or alkaline earth metal salts and, particularly, calcium, magnesium, sodium lithium, zinc, potassium, silicon, phosphorus, and iron salts.

The phrase "pharmaceutically acceptable carrier" is art-recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body.

Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerol, glycerides, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. In one embodiment, the pharmaceutically acceptable carrier is suitable for intravenous administration. In another embodiment, the pharmaceutically acceptable carrier is suitable for locoregional injection.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl, and propyl esters.

The dosage form of compositions described herein is not particularly limited. In certain embodiments, the composition is formulated as a topical, such as a cream or an ointment. In certain embodiments, the composition is formulated as a gel. In certain embodiments the composition is formulated as a suppository.

In certain embodiments, a suppository formulation comprises one or two polyglutamic acid compounds, a solubilizer, a humectant, a surfactant, and/or one or more suppository bases. An emollient can also be included in a suppository formulation. An example of a solubilizer is water. An example of a humectant is glycerin. An example of a surfactant is polysorbate 80. Examples of suppository bases are PEG4000, Gelucire 43/01, PEG3350, witepsol W-35®, and saturated fatty acids glycerides $C_{12}$-$C_{18}$. An example of an emollient is softisan 378. The one or two polyglutamic acid compounds have molecular weights ranging from 50 kDa to 2000 kDa. For examples, the molecular weight of a polyglutamic acid compound can be 50 kDa, 100 kDa, 150 kDa, 200 kDa, 250 kDa, 300 kDa, 350 kDa, 400 kDa, 450 kDa, 500 kDa, 550 kDa, 600 kDa, 650 kDa, 700 kDa, 750 kDa, 800 kDa, 850 kDa, 900 kDa, 950 kDa, 1000 kDa, 1050 kDa, 1100 kDa, 1150 kDa, 1200 kDa, 1250 kDa, 1300 kDa, 1350 kDa, 1400 kDa, 1450 kDa, 1500 kDa, 1550 kDa, 1600 kDa, 1650 kDa, 1700 kDa, 1750 kDa, 1800 kDa, 1850 kDa, 1900 kDa, 1950 kDa, or 2000 kDa. The weight percentage (% w/w) of each polyglutamic acid compound in any of the compositions described herein is not particularly limited and can range from about 0.01% to about 1%. For example, it can be 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, 0.30%, 0.31%, 0.32%, 0.33%, 0.34%, 0.35%, 0.36%, 0.37%, 0.38%, 0.39%, 0.40%, 0.41%, 0.42%, 0.43%, 0.44%, 0.45%, 0.46%, 0.47%, 0.48%, 0.49%, 0.50%, 0.51%, 0.52%, 0.53%, 0.54%, 0.55%, 0.56%, 0.57%, 0.58%, 0.59%, 0.60%, 0.61%, 0.62%, 0.63%, 0.64%, 0.65%, 0.66%, 0.67%, 0.68%, 0.69%, 0.70%, 0.71%, 0.72%, 0.73%, 0.74%, 0.75%, 0.76%, 0.77%, 0.78%, 0.79%, 0.80%, 0.81%, 0.82%, 0.83%, 0.84%, 0.85%, 0.86%, 0.87%, 0.88%, 0.89%, 0.90%, 0.91%, 0.92%, 0.93%, 0.94%, 0.95%, 0.96%, 0.97%, 0.98%, 0.99%, 1%, or more, or any value therebetween. The weight percentages (% w/w) of the solubilizer, the humectant, the surfactant, the one or more suppository bases, and the emollient in the suppository formulation are also not particularly limited and can range, respectively, from 1% to 100%, from about 0.1% to 11.4%, from 0.1% to 1.4%, from 0% to 100%, and from 0% to 100%. The amount of the polyglutamic acid compounds, the solubilize, the humectant, the surfactant, the suppository bases and/or the emollient are in a synergistic ratio. As used herein, a "synergistic ratio" refers to a ratio that elicits an unexpectedly superior pharmacological and physiological effect in a subject. An example of the synergistic ratio of the amount of the polyglutamic acid compound to the amount of the solubilizer to the amount of the humectant to the amount of the surfactant, and to the amount of the suppository base is 5:396:50:28:1521.

In certain embodiments, a suppository formulation comprises only one polyglutamic acid compound. In certain embodiments, the compound has a molecular weight of 100 kDa, 700 kDa, or 2000 kDa. In certain embodiments, a suppository formulation contains a solubilizer, a humectant, a surfactant, and a suppository base. In certain embodiments, the solubilizer is water, the humectant is glycerin, the surfactant is polysorbate 80, and the suppository base is saturated fatty acids glycerides $C_{12}$-$C_{18}$.

In certain embodiments, a suppository formulation comprises two polyglutamic acid compounds. In certain embodiments, the compounds have molecular weights of 100 kDa and 700 kDa.

In certain embodiments, suppository formulations can be disintegrated between 5-10 minutes, between 10-20 minutes, or between 20-30 minutes. In certain embodiments, a suppository formulation can be administered every two days, every three days, every four days, every five days, every six days, every week, every eight days, every nine days, every ten days, every two weeks, every month, or more to provide fast and long-lasting relief of the symptoms of vaginal dryness and the symptoms associated with menopause.

While the present invention has been described in some detail for purposes of clarity and understanding, one will appreciate that various changes in form and detail can be made without departing from the true scope of the invention.

EXAMPLES

Example 1

In one example, polyglutamic acid (mw: 100 kDa; 5 mg; 0.25% w/w) was mixed with water (396 mg; 19.8% w/w), glycerin (50 mg; 2.5% w/w), polysobrate 80 (28 mg; 1.4% w/w), and saturated fatty acids glycerides $C_{12}$-$C_{18}$ (1521 mg; 76.04% w/w) to yield a white suppository. A dissolution study of the suppository was conducted by using a phosphate buffer that has a pH range of about 4.2-4.5, which is within a range of normal vaginal pH (3.8-5.0). Percentages of polyglutamic acid in the buffer at hour 0.5, hour 0.75, hour 1, hour 2, hour 3, hour 6, hour 24, hour 30, and hour 48 were determined. The dissolution data are shown in Table 1 below.

TABLE 1

Dissolution Data

| Time (hr) | % Dissolved Average (n = 3) | Std Dev | % RSD |
|---|---|---|---|
| 0.5 | 67.16 | 13.24 | 19.7 |
| 0.75 | 68.27 | 19.91 | 29.2 |
| 1 | 72.97 | 19.12 | 26.2 |
| 2 | 88.21 | 9.90 | 11.2 |
| 3 | 98.09 | 1.78 | 1.8 |
| 4 | 100.01 | 4.19 | 4.2 |
| 24 | 101.83 | 3.25 | 3.2 |
| 30 | 100.64 | 3.09 | 3.1 |
| 48 | 102.85 | 3.13 | 3.0 |

It was observed that the suppository completely disintegrated within 30 minutes. The data shows that 67% of the polyglutamic acid compound was dissolved in 30 minutes and the polyglutamic acid compound was completely dissolved in the buffer at hour 3. Unexpectedly, a steady dissolution was observed from hour 0.5 to hour 3. Also unexpectedly, 100% of the polyglutamic acid compound remained in the buffer at hour 48, indicating that the compound is stable in a vaginal tissue and therefore, can moisturize the vaginal tissue for more than 2 days once administered. These unexpected results demonstrate that the composition can provide fast and long-lasting relief of the symptoms of vaginal dryness.

Example 2

The vaginal suppository composition described in example 1 above will be studied to evaluate its short-term stability as compared to a placebo prototype composition. The placebo composition will be identical to the vaginal suppository composition except that the former does not contain any polyglutamic acid compound. Both compositions will be placed on ICH stability at 2-8° C. and 25° C./60% RH conditions for 3 months. At the end of month 1 and month 2, the stability of the vaginal suppository composition will be evaluated by visual appearance and the amount of the polyglutamic acid compound remained in the composition. At the end of month 3, the stability of the vaginal suppository composition will be evaluated by, in addition to visual appearance and the amount of polyglutamic acid remaining in the composition, the amount of the polyglutamic acid compound dissolved. As to the placebo composition, its stability will be evaluated by visual appearance and placebo interference at the end of each month.

Example 3

An assay will be conducted where an in vitro vaginal tissue test apparatus will be used to test the activity and efficacy of varying polymer lengths of polyglutamic acid compounds. The varying polyglutamic acid compounds (i.e., with different n values) will be applied to the test apparatus, and their ability to penetrate into the various tissue layers of the vaginal wall will be correlated with their n value (i.e., the number of monomers in the polyglutamic acid compound), and the relative effect on vaginal moisture. In addition, compositions having varying concentrations of polyglutamic acid compounds with different polymer chain lengths (i.e., different n values) will be tested to ascertain the effect on vaginal moisture and penetration into vaginal tissue layers.

Example 4

Certain compositions described herein will be tested for their effects on the vaginal epithelium in a postmenopausal rat model.

Thirty female Wistar/Sprague rats (eight-week-old) will be purchased from the Firat University Experimental Animal Center. All rats will be individually housed under clean conditions with controlled temperature, humidity, and light (12-h light-dark cycle) and provided a standard commercial diet and water ad libitum. All experimental procedures will follow the guidelines established by the Use of Laboratory Animals and will be approved by the Animal Care and Use Committee of Firat University.

Rats that exhibited regular 4-days oestrous cycle will be chosen for the experiment. The rats will be divided into seven groups as shown in Table 2. After one adaptation period, rats will be ovariectomized (OVX) or given a sham operation (control) under anesthesia. The same weight of adipose tissue will be removed from rats in the control group. After the surgery, the vaginal smears will be assessed daily. Only rats whose vaginal smears that have exhibited regular 4-days cycles (before and after sham/OVX) and rats that exhibited constant leukocytes (after OVX) will be used (10 rats for each group). The rest of rats will be dosed intra-vaginally or orally with the same volume of placebo (vehicle) gel as rats that received a composition. The body weights of rats will be measured weekly.

TABLE 2

Study groups

| Groups | Source | HED | Animal dose (per rat/day) (n = 10 per arm)* |
|---|---|---|---|
| 1 | Saline | — | — |
| 2 | OVX | — | — |
| 3 | OVX+ | 5 mg | 0.51 mg/kg BW |
| 4 | OVX+ | 50 mg | 5.14 mg/kg BW |
| 5 | OVX+ | 500 mg | 51.42 mg/kg BW |
| 6 | OVX+ | 5000 mg | 514.16 mg/kg BW |
| 7 | OVX+ | 50 g | 0.52 g/kg BW |

*Doses of products were converted by allometric scaling, which takes into account differences in body surface area to calculate equivalent doses for rat by the following calculation, assuming an 60 kg human: RD = HED(g)/60 kg*6.17 (For example: (50 mg/60)*6.17 = 5.14 mg/kg BW); where RD is the rat dosage of products, HED is the human equivalent dosage of products, and 6.17 is the conversion factor to convert a human dosage to a rat dosage On day 15, the treatment effect of each composition for vaginal atrophy will be determined by a vaginal smear obtained from each rat, with a histological examination of a vaginal tissue. Vaginal smears will be fixed and detected, the expression of leukocyte esterase, $\beta$-glucuronidase, and coagulase will be used to determine the effect of each composition on vaginal microecosystem. Then all rats will be sacrificed by cervical dislocation and their vagina and uterus will be removed. The wet weight of each uterus will be determined once they will be carefully cleaned of any adherent tissue. To minimize variability due to dissection, all uteri will be dissected above the cervix at the same distance. The vaginal tissue will be then removed and will be cut into 1 mm×1 mm×2 mm sections, stained with 2.5% glutaraldehyde. Some vaginal samples will be taken and processed for histological examination by standard procedures (4-5 μm sections stained with haematoxylin plus eosin).

The repair capacity of each composition will be detected by Western blot. Vaginal VEGF, p-AKT, COX-2, ERα, and ERβ will be detected by Western blot method. For Western blot, proteins will be separated in 10% polyacrylamide gel, electrotransferred topolyvinylidene fluoride membranes, and the bands will be blocked in 5% dried milk for 1 hour at room temperature and incubated with different primary antibodies (1:1000). The incubation will be carried out in PBS supplemented with 5% skim milk powder. After washing with Tris-Buffered Saline (TBS) containing 0.1% Tween-20 (TBS-T), the membranes will be further incubated with an anti-rabbit IgG antibody conjugated with horseradish peroxidase at room temperature for 1 hour. After washing with TBS-T, antigen-antibody complex will be visualized by using an enhanced-chemiluminescence-detection kit.

The invention claimed is:

1. A method for treating vaginal dryness of pre-menopause and post-menopause, maintaining a healthy level of vaginal moisture, or treating and/or ameliorating one or more symptoms of menopause comprising administering a vaginal composition to a subject, wherein the vaginal composition is in the form of a suppository formulation and wherein the suppository formulation comprises one or more polyglutamic acid compounds, a suppository base, and a pharmaceutically acceptable carrier, wherein one of the one or more polyglutamic acid compounds has a molecular weight of 100 kDa and is present in a weight percentage of about 0.01% to about 1% of the total weight of the composition, and wherein the one or more symptoms of menopause are vaginal dryness, vaginal itching, vaginal burning, and/or pain associated with sexual activity.

2. The method of claim 1, wherein the one or more polyglutamic acid compounds comprises a first polyglutamic acid compound and a second polyglutamic acid compound.

3. The method of claim 2, wherein the one or more polyglutamic acid compounds further comprises a third polyglutamic acid compound.

4. The method of claim 2, wherein the first polyglutamic acid compound has an n value that is less than an n value of the second polyglutamic acid compound, wherein the n value is the number of glutamic acid monomers linked together to form each polyglutamic acid compound.

5. The method of claim 3, wherein the first polyglutamic acid compound has an n value that is less than an n value of the second polyglutamic acid compound, and the third polyglutamic acid compound has an n value that is greater than the n value of the second polyglutamic acid compound, wherein the n value is the number of glutamic acid monomers linked together to form each polyglutamic acid compound.

6. The method of claim 1, wherein the suppository formulation comprises one or two polyglutamic acid compounds.

7. The method of claim 6, wherein the suppository formulation further comprises a solubilizer, a humectant, and a surfactant.

8. The method of claim 7, wherein the amount of the polyglutamic acid compounds, the solubilizer, the humectant, the surfactant, and the suppository bases are in a synergistic ratio by weight.

9. The method of claim 6, wherein the suppository formulation comprises one polyglutamic acid compound.

10. The method of claim 9, wherein the suppository formulation further comprises a solubilizer, a humectant, and a surfactant.

11. The method of claim 10, wherein the solubilizer is water, the humectant is glycerin, the surfactant is polysorbate 80, and the suppository base is saturated fatty acids glycerides $C_{12}$-$C_{18}$.

12. The method of claim 4, wherein the first polyglutamic acid compound has a molecular weight of 100 kDa and the second polyglutamic acid compound has a molecular weight of 700 kDa.

13. The method of claim 12, wherein the suppository formulation further comprises a solubilizer, a humectant, and a surfactant.

14. The method of claim 13, wherein the solubilizer is water, the humectant is glycerin, the surfactant is polysorbate 80, and the suppository base is saturated fatty acids glycerides $C_{12}$-$C_{18}$.

15. The method of claim 1, wherein the method is for treating the vaginal dryness of pre-menopause and post-menopause, and wherein the suppository formulation is administered to a subject's vaginal cavity.

16. The method of claim 15, wherein the suppository formulation comprises only one polyglutamic acid compound.

17. The method of claim 15, wherein the suppository formulation comprises a first polyglutamic acid compound and a second polyglutamic acid compound.

18. The method of claim 1, wherein the method is for maintaining a healthy level of vaginal moisture, and wherein the suppository formulation is administered to a subject's vaginal tissue.

19. The method of claim 1, wherein the method is for treating and/or ameliorating one or more symptoms of menopause, and wherein the suppository formulation is administered to a subject's vaginal tissue.

20. A suppository formulation comprising a polyglutamic acid compound, a solubilizer, a humectant, a surfactant, and a suppository base, wherein the amount of the polyglutamic acid, the amount of a solubilizer, the amount of a humectant, the amount of the surfactant, and the amount of the suppository base are in a ratio of 5:396:50:28:1521 by weight, wherein the polyglutamic acid has a molecular weight of 100 kDa, the solubilizer is water, the humectant is glycerin, the surfactant is polysorbate 80, and the suppository base is saturated fatty acids glycerides $C_{12}$-$C_{18}$.

21. The suppository formulation of claim 20, wherein the suppository formulation disintegrates in the vaginal environment within 30 minutes.

22. A method for treating vaginal dryness of pre-menopause and post-menopause, maintaining a healthy level of vaginal moisture, or treating and/or ameliorating one or more symptoms of menopause comprising administering a vaginal composition to a subject, wherein the vaginal composition is in the form of a suppository formulation and the suppository formulation comprises a first polyglutamic acid compound, a second polyglutamic acid compound, a third polyglutamic acid compound, a suppository base, and a pharmaceutically acceptable carrier, wherein the first polyglutamic acid compound has an n value that is less than an n value of the second polyglutamic acid compound, and the third polyglutamic acid compound has an n value that is greater than the n value of the second polyglutamic acid compound, wherein the n value is the number of glutamic acid monomers linked together to form each polyglutamic acid compound, and wherein the first polyglutamic acid compound has the n value of between about 300 and 500, the second polyglutamic acid compound has the n value between about 1,000 and 10,000, and the third polyglutamic acid compound has the n value between about 20,000 and 30,000, and wherein the one or more symptoms of menopause are vaginal dryness, vaginal itching, vaginal burning, and/or pain associated with sexual activity.

* * * * *